US 007888523B2

(12) United States Patent
Du Preez

(10) Patent No.: US 7,888,523 B2
(45) Date of Patent: Feb. 15, 2011

(54) PREPARATION OF PLATINUM(II) COMPLEXES

(75) Inventor: Jan Gysbert Hermanus Du Preez, Port Elizabeth (ZA)

(73) Assignee: Platco Technologies (Proprietary) Limited, Port Elizabeth (ZA)

( * ) Notice: Subject to any disclaimer, the term of this patent is extended or adjusted under 35 U.S.C. 154(b) by 0 days.

(21) Appl. No.: 12/508,466

(22) Filed: Jul. 23, 2009

(65) Prior Publication Data

US 2009/0299085 A1 Dec. 3, 2009

Related U.S. Application Data

(63) Continuation of application No. 11/661,785, filed as application No. PCT/IB2005/000570 on Mar. 7, 2005, now Pat. No. 7,589,225.

(60) Provisional application No. 60/606,119, filed on Sep. 1, 2004, provisional application No. 60/606,124, filed on Sep. 1, 2004.

(51) Int. Cl.
C07F 15/00 (2006.01)
A61K 31/28 (2006.01)

(52) U.S. Cl. .................... 556/137; 556/136; 548/101; 546/2; 514/492

(58) Field of Classification Search ................ 556/136, 556/137; 548/101; 546/2; 514/492
See application file for complete search history.

(56) References Cited

U.S. PATENT DOCUMENTS

| 4,169,846 | A | 10/1979 | Kidani et al. |
|---|---|---|---|
| 4,536,571 | A | 8/1985 | Stockel et al. |
| 5,281,447 | A | 1/1994 | Brady et al. |
| 5,290,961 | A | 3/1994 | Okamoto et al. |
| 5,338,874 | A | 8/1994 | Nakanishi et al. |
| 5,420,319 | A | 5/1995 | Okamoto et al. |
| 5,716,988 | A | 2/1998 | Ibrahim et al. |
| 5,959,133 | A | 9/1999 | Ohnishi |
| 6,376,057 | B1 | 4/2002 | Akao et al. |
| 6,866,857 | B1 | 3/2005 | Mauvernay |
| 7,070,796 | B1 | 7/2006 | Ibrahim et al. |
| 7,122,668 | B2 | 10/2006 | Barenholz et al. |
| 7,208,616 | B2 | 4/2007 | Menez et al. |
| 7,309,796 | B2 | 12/2007 | Pepels et al. |
| 7,351,846 | B2 | 4/2008 | Zák et al. |
| 2004/0186172 | A1 | 9/2004 | Ibrahim |
| 2006/0063833 | A1 | 3/2006 | Schridde et al. |
| 2006/0275331 | A1 | 12/2006 | Zaludek et al. |
| 2007/0073074 | A1 | 3/2007 | Zak et al. |
| 2007/0167643 | A1 | 7/2007 | Du Preez |
| 2007/0197811 | A1 | 8/2007 | Menez et al. |
| 2008/0064895 | A1 | 3/2008 | Du Perez |
| 2009/0312417 | A1 | 12/2009 | Du Preez |

FOREIGN PATENT DOCUMENTS

| EP | 0 115 929 | | 8/1984 |
|---|---|---|---|
| EP | 0 345 356 | A1 | 12/1989 |
| EP | 0 345 356 | A4 | 12/1989 |
| EP | 0 617 043 | B1 | 9/1994 |
| EP | 0 625 523 | B1 | 11/1994 |
| EP | 0 715 854 | B1 | 6/1996 |
| EP | 0 774 963 | B1 | 5/1997 |
| EP | 0 801 070 | B1 | 10/1997 |
| EP | 0 881 226 | B1 | 12/1998 |
| EP | 0 943 331 | B1 | 9/1999 |
| EP | 1 121 117 | B1 | 8/2001 |
| EP | 1 207 875 | B1 | 5/2002 |
| EP | 1 308 453 | A2 | 5/2003 |
| EP | 1 308 453 | A3 | 5/2003 |
| EP | 1 308 454 | B1 | 5/2003 |
| EP | 1 561 754 | B1 | 8/2005 |
| EP | 1 680 434 | B1 | 7/2006 |
| EP | 1 704 156 | | 9/2006 |
| GB | 2 210 039 | A | 6/1989 |
| JP | 5-301884 | A | 11/1993 |
| WO | WO-03/004505 | A1 | 1/2003 |
| WO | WO-2005/051966 | A1 | 6/2005 |
| WO | WO-2005/075489 | A1 | 8/2005 |
| WO | WO-2006/023154 | A1 | 3/2006 |
| WO | WO-2006/024897 | A1 | 3/2006 |
| WO | WO-2006/108428 | A1 | 10/2006 |
| WO | WO-2007/085957 | A1 | 8/2007 |

OTHER PUBLICATIONS

Bierbach, U. et al. (1998, e-pub. Jan. 31, 1998). "Modification of Platinum(II) Antitumor Complexes with Sulfur Ligands. 1. Synthesis, Structure, and Spectroscopic Properties of Cationic Complexes of the Types [PtCl(diamine)(L)]NO$_3$ and [{PtCl(diamine)}$_2$(L-L)](NO$_3$)$_2$ (L=Monofunctional Thioureau Derivative; L-L=Bifunctional Thioureau Derivative)," *Inorg. Chem.* 37(4):708-716.

Database CA [Online] Chemical Abstracts Service, Columbus, Ohio, US; Abel, Edward W. et al: "Platinum metal complexes of potentially chelating alkene thioether and selenoether ligands: the synthesis and dynamic nuclear magnetic resonance study of [MX2{E[(CH2)nCR:CR2]2}] (M=Pt or Pd; X=Cl, Br, or I; E=S or Se; n=2 or 3; R=H or Me) and the x-ray crystal structure of cis-diiodo(5-thi" retrieved from STN Database accession No. 1990:235576, Journal of the Chemical Society, Dalton Transactions: Inorganic Chemistry (1972-1999) (11):2315-2321, CODEN: JCDTBI; ISSN: 0300-9246, 1989 (Abstract only).

(Continued)

*Primary Examiner*—Porfirio Nazario Gonzalez
(74) *Attorney, Agent, or Firm*—Morrison & Foerster LLP

(57) ABSTRACT

This invention relates to a method for the preparation of a platinum(II) complex containing a neutral bidentate ligand, such as oxaliplatin. The method includes the step of reacting a halogenoplatinum complex containing a neutral bidentate ligand with an oxalate salt in a solvent, wherein more than 1 g/L of the oxalate salt is soluble in the solvent. The invention also relates to new platinum(II) complexes.

102 Claims, No Drawings

OTHER PUBLICATIONS

Database CA [Online] Chemical Abstracts Service, Columbus, Ohio, US; Abel, Edward W. et al: "Platinum metal complexes of potentially chelating alkene-thioether and alkene-selenoether ligands: synthesis and dynamic nuclear magnetic resonance study of [MX2{MeE(CH2)nCH=CH2}] (M=platinum or palladium; X=Cl, Br, or I; E=S or Se; n=2 or 3) and the x-ray structure of cis-dibromo(2-thia-6-heptene)platinum(II)," retrieved from STN Database accession No. 1990:56232, Journal of the Chemical Society, Dalton Transactions: Inorganic Chemistry (1972-1999) 11:2315-2321, CODEN: JCDTBI; ISSN: 0300-9246, 1989 (Abstract only).

Database CA [Online] Chemical Abstracts Service, Columbus, Ohio, US; Abel, Edward W. et al: "Synthetic, dynamic nuclear magnetic resonance and crystallographic studies of platinum cpmplexes containing silyl-substituted dialkenyl-thioether and -selenoether ligands," retrieved from STN Database accession No. 1995:114833, abstract, compound I & Journal of the Chemical Society, Dalton Transactions: Inorgamic Chemistry (1972-1999) 18:2637-2643, CODEN: JCDTBI; ISSN: 0300-9246, 1994 (Abstract only).

Database CA [Online] Chemical Abstracts Service, Columus, Ohio, US; Balakrishna, Maravanji S. et al: "Heterodifunctional ligands derived from monooxidized bis(phosphino)amines. Synthesis and transition metal (molybdenum(O), tungsten(O), rhodium(I), palladium(II), and platinum(II)) complexes of (diphenylphosphino)(diphenylphosphinothio lyl)- and (diphenylphosphino)(diphenylphosphinoselen oyl)phenylam," retrieved from STN Database accession No. 1993:685076, abstract & Inorganic Chemistry 32(25):5676-5681, CODEN: INOCAJ; ISSN: 0020-1669, 1993 (Abstract only).

Database CA [Online] Chemical Abstracts Service, Columbus, Ohio, US; Belletti, Daniele et al: "Reactivity of Ph2(2-C5H4N)Pse towards Ru3(CO)12 and mononuclear MCl2(PhCN)2 (M=Pd or Pt) complexes," retrieved from STN Database accession No. 2003:483190, Inorganic Chimica Acta 350:421-427, CODEN: ICHAA3; ISSN: 0020-1693, 2003 (Abstract only).

Database CA [Online] Chemical Abstracts Service, Columbus, Ohio, US; Bhasin, Kuldip K. et al: "2,5-Diselena-3,3,4,4-tetrafluorohexane and 2,5-diselena-1,1,1,6,6,6-hexafluorohexane and their platinum and palladium chloride complexes," retrieved from STN Database accession No. 1979:567640, Journal of Fluorine Chemistry 14(2):171-176, CODEN: JFLCAR; ISSN: 0022-1139, 1979 (Abstract only).

Database CA [Online] Chemical Abstracts Service, Columbus, Ohio, US; Clarke, M. L. et al: "First examples of M-Se-P-N-N heterocycles," retrieved from STN Database accession No. 2001:237332, Inorganic Chemistry Communications 4(3):115-118, CODEN: ICCOFP; ISSN:1387-7003, 2001 (Abstract only).

Database CA [Online] Chemical Abstracts Service, Columbus, Ohio, US; Harbron, Stephen K. et al: "Coordination chemistry of higher oxidation states. Part 24. Palladium(IV) and nickel(III) complexes of hybrid thio- and seleno-ether ligands," retrieved from STN Database accession No. 1987:589472, Inorganica Chimica Acta 130(1):43-47, CODEN: ICHAA3; ISSN: 0020-1693,1987 (Abstract only).

Database CA [Online] Chemical Abstracts Service, Columbus, Ohio, US; Kemmitt, Tim et al: "Chelating ditelluroether complexes of palladium and platinum: synthesis and multinuclear NMR studies. Structure of dibromo(meso-1,3-bis(phenyltelluro)propane )palladium(II): [Pd{meso-PhTe(CH2)3TePh}Br2]," retrieved from STN Database accession No. 1989:87401, Inorganic Chemistry 28(4):692-696, CODEN: INOCAJ; ISSN: 0020-1669, 1989 (Abstract only).

Database CA [Online] Chemical Abstracts Service, Columbus, Ohio, US; Khanna, Anju et al: "Synthesis and multinuclear NMR studies of 3-aminopropyl(aryl)chalcogenides, NH2CH2CH2CH2Ear (E=Se, Te), and their complexes with Pt(II) and Pd(II)," retrieved from STN Database accession No. 1995:569289. Journal of Organometallic Chemistry 494(1-2):199-204, CODEN: JORCAI; ISSN:0022-328X, 1995 (Abstract only).

Database CA [Online] Chemical Abstracts Service, Columbus, Ohio, US; Khuzaie, Rula F. et al: "Screening for anticomplementary activity of some platinum (II) and palladium (II) complexes with various donor ligands and anions," XP002317068 retrieved from STN Database accession No. 2002:445382, Oriental Journal of Chemistry 18(1):1-6, CODEN: OJCHEG; ISSN: 0970-020X, 2002 (Abstract only).

Database CA [Online] Chemical Abstracts Service, Columbus, Ohio, US; Knorr, Michael et al: "Synthesis and molecular structures of platinum and mercury complexes chelated by (phenylthiomethyl)silane ligands," retrieved from STN Database accession No. 2004:973319, Zeitschrift Fuer Anorganische Und Allegemeine Chemie 630(12):1955-1961, CODEN: ZAACAB; ISSN: 0044-2313, Oct. 21, 2004 (Abstract only).

Database CA [Online] Chemical Abstracts Service, Columbus, Ohio, US; Mizuno, Masagi: "Linear chain compound bisoxalatoplatinate complexes," XP002317074 retrieved from STN Database accession No. 1989:432596, Kagaku Kogyo Shiryo (Tsukuba, Japan) 23(5):201-216, CODEN: KKSHEP; ISSN: 0288-8882, 1989 (Abstract only).

Database CA [Online] Chemical Abstracts Service, Columbus, Ohio, US; Prignano, Andrea L. et al: "Silica-anchored bis(trialkylphosphine) platinum oxalate: a photogenerated catalyst for olefin hydrosilation," XP002317070 retrieved from STN Database accession No. 1987:77537, Monatshefte Fuer Chemie 117(5):617-619, CODEN: MOCMB7; ISSN: 0026-9247, 1986 (Abstract only).

Database CA [Online] Chemical Abstracts Service, Columbus, Ohio, US; Puniyani, Sushil et al: "Platinum (II) complexes of cyclohexanone and cyclopentanone thiosemicarbazones," XP002317071 retrieved from STN Database accession No. 1985:447222 Indian Journal of Chemistry, Section A: Inorganic, Physical, Theoretical & Analytical 24a(3):240-241, CODEN: IJCADU; ISSN: 0376-4710, 1985 (Abstract only).

Database CA [Online] Chemical Abstracts Service, Columbus, Ohio, US; Rashan, Luay J. et al: "In vitro antitumor activity of platinum (II) complexes with various nitrogen containing ligands," XP002317069 retrieved from STN Database accession No. 1998:522331, Biologia (Bratislava) 53(3):349-352, CODEN: BLOAAO; ISSN: 0006-3088, 1998 (Abstract only).

Database CA [Online] Chemical Abstracts Service, Columbus, Ohio, US; Song, Rita et al: "Synthesis and selective tumor targeting properties of water soluble porphyrin-Pt(II) conjugates," [Erratum to document cited in CA137:362598] XP002317067 retrieved from STN Database accession No. 2002:85473, Journal of Inorganic Biochemistry 92(3-4):200, CODEN: JIBIDJ; ISSN: 0162-0134, 2002. Erratum found in Database CA [Online] Chemical Abstracts Service, Columbus, Ohio, US; Song, Rita et al: "Synthesis and selective tumor targeting properties of water soluble porphyrin-Pt(II) conjugates," retrieved from STN Database accession No. 2002:249587 Journal of Inorganic Biochemistry 89(1-2):83-88, CODEN: JIBIDJ; ISSN: 0162-0134, 2002 (Abstract only).

Database CA [Online] Chemical Abstracts Service, Columbus, Ohio, US; Syamal, A. et al: "Synthesis of new platinum (II) complexes with ethanethiolamine, o-aminothiophenol and bidentate carboxylic acids," XP002317072 retrieved from STN Database accession No. 1983: 209058, Revue De Chimie Minerale 20(1):123-128, CODEN: RVCMA8; ISSN: 0035-1032, 1983 (Abstract only).

Database CA [Online] Chemical Abstracts Service, Columbus, Ohio, US; Uttecht, J.-G. et al: "Synthesis, vibrational spectra and normal coordinate analysis of (n-Bu4N)2 [Pt(SCN)n(ox)], n=2,4, and crystal structure of [(C5H5N)2CH2][Pt(SCN)4(ox)]," XP002317073 retrieved from STN Database accession No. 2002:781520, Zeitschrift Fuer Naturforschung, B: Chemical Sciences 57(9):1036-1042, CODEN: ZNBSEN; ISSN: 0932-0776, 2002 (Abstract only).

Gladiali, S. et al. (1988). "Synthesis, Structure, and Dynamic Behaviour of Transition Metal Chelate Complexes with Atropismeric Dithioether Ligands" *Eur. J. Inorg. Chem.* pp. 113-118.

Gümüs, F. et al. (2003). "Synthesis, Characterization and In Vitro Cytotoxic, Mutagenic and Antimicrobial Activity of Platinum(II) Complexes with Substituted Benzimidazole Ligands," *J. Inorg. Biochem.* 94(3):255-262.

International Preliminary Report on Patentability mailed on Nov. 23, 2005, for PCT Patent Application No. PCT/IB2004/003855, filed on Nov. 24, 2003, 20 pages.

International Preliminary Report on Patentability mailed on Mar. 1, 2007, for PCT Patent Application No. PCT/IB2005/000570, filed on Mar. 7, 2005, 28 pages.

International Preliminary Report on Patentability mailed on Aug. 5, 2008, for PCT Patent Application No. PCT/IB2007/000213, filed on Jan. 30, 2007, 6 pages.

International Search Report mailed on Mar. 23, 2005 for PCT Patent Application No. PCT/IB2004/003855, filed on Nov. 24, 2004, 5 pages.

International Search Report mailed on Aug. 2, 2005, for PCT Patent Application No. PCT/IB2005/000570, filed on Mar. 7, 2005, 7 pages.

International Search Report mailed on Jun. 11, 2007, for PCT Patent Application No. PCT/IB2007/000213, filed on Jan. 30, 2007, 2 pages.

Khokhar, A.R. et al. (1985). "The Synthesis and Antitumor Properties of a Series of Water Soluble Carboxylato-(1,2-diaminocyclohexane) Platinum(II) Complexes", *Inorganica Chimica Acta* 108:63-66.

Mizuno, M. (1988). "Linear Chain Compound Bisoxalatoplatinate Complexes," *Kagaku Kogyo Shiryo* 23(5):201-216. (Japanese language only.) [See English abstract citation above: Database CA [Online] . . . STN Database accession No. 1989:432596.]

Pasini, A., et al. (1989). "A New Synthetic Method for Diaminomalonatoplatinum Type Complexes and the Unexpected Behavior of [PtCl$_2$(trans-dach)]," *Inorganic Chemical* 152, Italy (1988), pp. 19-20.

Puniyani, S. et al. Platinum(II) Complexes of Cyclohexanone and Cyclopentanone Thiosemicarbazones, *India Journal of Chemistry, Section A: Inorganic, Physical, Theoretical & Analytical* 24A(3):240-241.

Reedijk, J. (1999, e-pub. Aug. 21, 1999). "Why Does Cisplatin Reach Guanin-N7 with Competing S-Donor Liganded Available in the Cell?" *Chem. Rev.* 99(9):2499-2510.

Schanz, H-J. et al. (2003). "Improved Resolution Methods for (*R,R*)- and (*S,S*)-cyclohexane-1,2-diamine and (*R*)- and (*S*)-BINOL", *Tetrahedron: Asymmetry* 14(18):2763-2769.

Shriver, D.F., ed. (1979). "Partially Oxidized Potassium Bis(oxalate)palatinate," *Inorganic Syntheses*, vol. 19, John Wiley and Sons: New York, NY, one page.

Thornber, C.W. (1979). "Isosterism and Molecular Modification in Drug Design," *Chemical Society Reviews* [Chemical Society, London, GB] 8(4):563-580.

Written Opinion mailed on Mar. 21, 2006, for PCT Patent Application No. PCT/IB2004/003855, filed on Nov. 24, 2004, 12 pages.

Written Opinion mailed on Mar. 1, 2007, for PCT Patent Application No. PCT/IB2005/000570, filed on Mar. 7, 2005, 10 pages.

Written Opinion mailed on Aug. 5, 2008, for PCT Patent Application No. PCT/IB2007/000213, filed on Jan. 30, 2007, 5 pages.

U.S. Appl. No. 12/162,745, filed Jan. 30, 2007, for De Preez.

Syamal, A et al. (Dec. 20, 1982). "Platinum (II and IV) Complexes with NS and No Donor Ligands," *Current Science* 51(24):1153-1155.

PREPARATION OF PLATINUM(II) COMPLEXES

CROSS-REFERENCE TO RELATED APPLICATIONS

This application is a continuation of U.S. patent application Ser. No. 11/661,785 (now U.S. Pat. No. 7,589,225), having a 371 filing date of Mar. 1, 2007, which is a National Phase filing under 35 U.S.C. §371 of International Application No. PCT/IB2005/000570, filed on Mar. 7, 2005, which claims priority to U.S. Provisional Patent Application Nos. 60/606,119, filed on Sep. 1, 2004, and 60/606,124, filed on Sep. 1, 2004. The contents of these applications are incorporated herein by reference in their entireties.

BACKGROUND OF THE INVENTION

This invention relates to the preparation of a platinum(II) complexes containing a neutral bidentate ligand, such as cis-oxalato(trans-l-1,2-cyclohexanediamine)platinum(II) (also known as oxaliplatin), which has become increasingly important due to its anticancer activity.

Dicarboxylatoplatinum(II) complexes (such as oxaliplatin) containing a neutral bidentate ligand ("non-leaving group") have in the past been synthesized by way of a process that utilizes a silver salt to remove halide ions from the complex. The use of a silver compound in the process results in numerous contaminants, which must be removed by further processes in order to achieve purity that is suitable for anti-cancer pharmaceutical agent purposes.

Oxaliplatin and its pharmaceutical properties were first disclosed by Kidani et. al. in J Med Chem, 1978, 21, 13135 and in U.S. Pat. No. 4,169,846. In this patent a halogenoplatinum compound is used as the starting material. Halide ions are removed by a silver salt, whereafter an oxalate is introduced, either as the free acid or a salt thereof.

In general, a method for the production of oxaliplatin is as set out below:

Step 1.

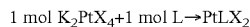

X=Cl, Br, I and L=trans-l-1,2-diaminocyclohexane

Step 2.

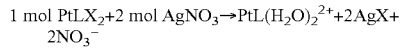

or

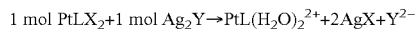

$Y=SO_4^{2-}$

Step 3.

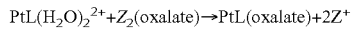

$Z=K^+$, $Na^+$ or $H^+$

U.S. Pat. No. 5,290,961 in the name of Tanaka Kikinzoku Kogyo K.K. teaches that the abovementioned method has the disadvantage that many impurities are incorporated into the products. These impurities include unreacted $PtLX_2$, $AgX$ and $Ag^+$. The presence of $PtLX_2$ is attributed to its generally insoluble nature in water. As a result, large quantities of water must be used in step 2 to dissolve $PtLX_2$. This prevents the AgX, even though it is insoluble in water, from being completely removed from the solution. U.S. Pat. Nos. 5,338,874 and 5,420,319, also in the name of Tanaka Klikinzoku Kogyo K.K., teach processes for the production of cis-oxalato(trans-l-1,2-diaminocyclohexane)platinum(II) with high optical purity which can be used as an active pharmaceutical ingredient of a carcinostatic agent. However, these processes also follow complicated multi-step pathways, making use of silver compounds which must also ultimately be removed from the process.

SUMMARY OF THE INVENTION

According to a first aspect of the invention there is provided a method for the preparation of a platinum(II) complex containing a neutral bidentate ligand, such as oxaliplatin, the method including the step of reacting a halogenoplatinum complex containing a neutral bidentate ligand, typically a halogenoplatinum(II) complex containing a neutral bidentate ligand, with an oxalate salt in a solvent, wherein more than 1 g/L of the oxalate salt is soluble in the solvent.

The solvent may be an aqueous solvent, a non-aqueous solvent or a mixed solvent system (by mixed solvent system is meant a solvent mixture containing a non-aqueous solvent and water).

Preferably, the halogenoplatinum(II) complex containing a neutral bidentate ligand is reacted with the oxalate at a molar ratio of greater than 1:1, typically between 1:1 to 1:15, preferably between 1:1 and 1:5.

The reaction typically takes place at a temperature in the range from 40 to 100° C., preferably from 50 to 100° C., most preferably from 60 to 90° C.

Preferably, the reaction takes place in a non-aqueous solvent or a mixed solvent system.

The non-aqueous solvent is preferably an organic liquid, typically an amide such as dimethylformamide (dmf).

The neutral bidentate ligand in the halogenoplatinum complex may be an amine such as 1,2-diaminocyclohexane, or the neutral bidentate ligand may contain donor atoms other than N, or N together with a donor atom other than N, typically S or Se, for example:

neutral bidentate heterocyclic amines with an S donor atom (for example thioethereal groups), such as:

1-alkyl/aryl-2-alkylthioalkyl/aryl heterocyclic amines, particularly imidazoles or pyridines, for example:
Ligand (i) 1-methyl-2-methylthiomethyl-imidazole
Ligand (ii) 1-methyl-2-methylthioethyl-imidazole
Ligand (iii) 1-methyl-2-methylthiopropyl-imidazole
Ligand (iv) 1-butyl-2-methylthiomethyl-imidazole
Ligand (v) 1-butyl-2-methylthioethyl-imidazole
Ligand (vi) 2-methylthiomethyl-pyridine
Ligand (vii) 2-methylthioethyl-pyridine
Ligand (viii) 2-methylthiopropyl-pyridine;
  aminoalkylthioalkyl/aryl compounds for example:
Ligand (ix) 1-amino-2-thiomethyl-ethane
Ligand (x) 1-amino-2-thioethyl-ethane;
  dithioethers for example:
Ligand (xi) 2,5-dithiahexane;
  diselenoethers for example:
Ligand (xii) 2,5-diselenohexane; etc.

The halogen in the halogenoplatinum(II) complex may be Cl, Br or I, preferably Cl.

New halogenoplatinum(II) complexes containing S or Se donor atoms which may be used in the method of the invention include:

Complex (xi) bis-chloro-(1-methyl-2-methylthiomethyl-imidazole)platinum(II)

Complex (xii) bis-chloro-(1-methyl-2-methylthioethyl-imidazole)platinum(II)

Complex (xiii) bis-chloro-(1-methyl-2-methylthiopropyl-imidazole)platinum(II)

Complex (xiv) bis-chloro-(1-butyl-2-methylthiomethyl-imidazole)platinum(II)

Complex (xv) bis-chloro-(1-butyl-2-methylthioethyl-imidazole)platinum(II).

Advantageously, the halogenoplatinum(II) complex containing a neutral bidentate ligand is optically pure.

The oxalate may be a metal oxalate other than silver oxalate or an organic oxalate salt.

In a first preferred embodiment of the invention, the oxalate is a metal oxalate other than silver oxalate, typically an alkali metal oxalate such as rubidium or cesium oxalate, preferably cesium oxalate, and the solvent is a mixed solvent system.

The mixed solvent system is preferably a mixture of an amide e.g. dimethylformamide (dmf) and water, preferably at a ratio of dmf to water of 60:40 by volume to 90:10 by volume, most preferably 70:30 by volume to 90:10 by volume.

Preferably, the solubility of the metal oxalate in the solvent is greater than 2 g/L, most preferably greater then 3 g/L, typically about 5 g/L.

Preferably, the halogenoplatinum(II) complex containing a neutral bidentate ligand is dissolved in the organic liquid such as dmf and thereafter water is added to provide a solvent which is a mixture of organic liquid and water. The metal oxalate may be dissolved in a mixture of organic liquid and water and added, typically drop-wise, to a solvent containing the halogenoplatinum(II) complex containing a neutral bidentate ligand.

The reaction typically takes place at a temperature in the range of 40 to 100° C., preferably 80 to 100° C., most preferably 90° C.

The halogenoplatinum(II) complex is preferably bis-chloro-(trans-l-1,2-diaminocyclohexane)platinum(II), most preferably cis-bis-chloro-(trans-l-1,2-diaminocyclohexane)platinum(II).

In the second preferred embodiment of the invention, the oxalate is an oxalate salt such as a tetraalkyl or arylammonium compound, for example a tetraethylammonium, tetrapropylammonium, tetrabutylammonium or tetraphenylphosphonium oxalate, preferably tetrabutylammonium oxalate, and the solvent is a mixed solvent system or a purely non-aqueous solvent system.

The mixed solvent system may be a mixture of a non-aqueous solvent such as dmf, and water, preferably at a ratio of dmf to water of 90:10 by volume to 95:5 by volume.

Preferably, the organic oxalate salt has a solubility in the solvent of greater than 2 g/L, more preferably greater than 10 g/L, more preferably greater than 50 g/L, most preferably more than 100 g/L, and may be about 300 g/L.

Preferably, the halogenoplatinum(II) complex containing a neutral bidentate ligand is dissolved in an organic liquid and the organic oxalate salt is dissolved in an organic liquid and added, typically drop-wise, to the solvent containing the halogenoplatinum(II) complex containing a neutral bidentate ligand.

Water may be added to the organic liquid after the cis-bis-halogeno(trans-l-1,2-diaminocyclohexane)platinum(II) has been dissolved in the organic liquid.

The reaction typically takes place at a temperature in the range of 30° C. to 90° C., preferably 50° C. to 70° C., most preferably 60° C.

The halogenoplatinum(II) complex is preferably bis-chloro-(trans-l-1,2-diaminocyclohexane)platinum(II), most preferably cis-bis-chloro(trans-l-1,2-diaminocyclohexane)platinum(II).

The invention also relates to a method for the preparation of an oxalatoplatinum(II) complex containing a neutral bidentate ligand, such as oxaliplatin, the method including the step of reacting a halogenoplatinum complex containing a neutral bidentate ligand, typically a halogenoplatinum (II) complex containing a neutral bidentate ligand, with a metal oxalate other than silver oxalate, in a mixed solvent system.

The invention further relates to a method for the preparation of an oxalatoplatinum(II) complex containing a neutral bidentate ligand, such as oxaliplatin, the method including the step of reacting a halogenoplatinum complex containing a neutral bidentate ligand, typically a halogenoplatinum(II) complex containing a neutral bidentate ligand, with an organic oxalate salt.

New halogenoplatinum(II) complexes having neutral bidentate ligands containing S or Se donor atoms include:

Complex (xi) bis-chloro-(1-methyl-2-methylthiomethyl-imidazole)platinum(II)

Complex (xii) bis-chloro-(1-methyl-2-methylthioethyl-imidazole)platinum(II)

Complex (xiii) bis-chloro-(1-methyl-2-methylthiopropyl-imidazole)platinum(II)

Complex (xiv) bis-chloro-(1-butyl-2-methylthiomethyl-imidazole)platinum(II)

Complex (xv) bis-chloro-(1-butyl-2-methylthioethyl-imidazole)platinum(II).

The above new complexes may be used in methods of treating cancer in patients, and in methods of manufacturing medicaments for treating cancer in patients.

DETAILED DESCRIPTION OF EMBODIMENTS

Optically pure trans-l-1,2-diaminocyclohexane is used to prepare an optically pure halogenoplatinum complex containing a neutral bidentate ligand in the form of cis-bis-halogeno(trans-l-1,2-diaminocyclohexane)platinum(II), from $K_2PtX_4$ where X=Cl, Br, I, preferably X=Cl.

The optically pure trans-l-1,2-diaminocyclohexane may be prepared by dissolving trans-1,2-diaminocyclohexane in water and adding l-tartaric acid to the solution by stirring continuously at 90° C. When all the tartaric acid is dissolved, glacial acetic acid is added drop-wise while stirring. The mixture is heated for 1 hour at 90° C. whereafter it is cooled to room temperature. The resultant white l-1,2-diaminocyclohexane-tartrate is filtered and washed and oven dried. The salt is then crystallized out of the hot water and cooled. The recrystallized l-1,2-diaminocyclohexane-l-tartrate is added to sodium hydroxide and dissolved in water. Once the amine has dissolved it is extracted with dichloromethane. The extracted dichloromethane portions are added together and dried with anhydrous sodium sulphate. Most of the solvent is removed by vacuum distillation. The last portion of solvent may be removed at atmospheric pressure to avoid the amine from distilling under vacuum, using an air condenser.

The optically pure trans-l-1,2-diaminocyclohexane is then reacted with a platinum(II) compound such as $K_2PtX_4$ where X is a halide such Cl, Br or I, typically $K_2PtCl_4$, to form cis-bis-halogeno(trans-l-1,2-diaminocyclohexane)platinum (II), typically cis-bis-chloro-(trans-l-1,2-diaminocyclohexane)platinum(II). This method is described in Inorganica Chimica Acta (1985) 108: pp 63-66 (the content of which is incorporated herein by reference).

The optically pure cis-bis-halogeno(trans-l-1,2-diaminocyclohexane)platinum(II), typically cis-bis-chloro-(trans-l-1,2-diaminocyclohexane)platinum(II), is then reacted with a oxalate salt in a solvent. In prior art methods, such as those discussed in the background to the invention, silver ions are used in the production of oxaliplatin. Such reactions take place in an aqueous solution and silver chloride (AgCl) is formed as a by-product of the reaction. Less than 1 g/L of the cis-bis-chloro-(trans-l-1,2-diaminocyclohexane)platinum (II) is soluble in the aqueous solution, and the driving force of the reaction is the insolubility of the AgCl (which must be removed from the solution by filtration). According to an aspect of the invention, the inventor has found that it is advantageous to carry out the reaction of the present invention in a solvent system in which more than 1 g/L of the oxalate salt is soluble. In this system, the driving force of the reaction is the fact that the oxalate ion in solution is dianonic and chelates to Pt(II) resulting in a thermodynamically more favourable complex than chloride. Preferably, at least 5 g/L of cis-bis-halogeno(trans-l-1,2-diaminocyclohexane)platinum(II) and oxalate salt, respectively, are in solution. A further advantage is that the insoluble AgCl by-product is not formed and it is possible to remove unwanted by-products by suitable washing. The solvent may be an aqueous solvent, but is preferably a non-aqueous solvent or a mixed solvent system (by mixed solvent system is meant a solvent mixture containing a non-aqueous solvent and water).

In a first preferred embodiment of the invention, cis-bis-halogeno(trans-l-1,2-diaminocyclohexane)platinum(II), preferably where the halogen is chloride, is dissolved in dimethylformamide (dmf) by heating the solvent in the temperature range of 40 to 100° C., preferably 80 to 100° C., most preferably 90° C. Water is then added to the solution to provide a mixed solvent system, in this case a mixture of dmf and water, at a temperature in the range of 40 to 100° C., preferably 80 to 100° C., most preferably 90° C. which is a hot yellow solution of cis-bis-chloro-(trans-l-1,2-diaminocyclohexane)platinum(II). One molar equivalent of a metal oxalate, other than silver oxalate, e.g. rubidium or cesium oxalate (preferably cesium oxalate) is dissolved in a mixed solvent system comprising a mixture of dmf and water and added drop-wise to the hot yellow solution. The ratio of dmf to water is 87:13. The cis-bis-chloro-(trans-l-1,2-diaminocyclohexane)platinum(II) has a solubility of 10 g/L in the solution and the cesium oxalate has a solubility of 5 g/L in the solution. The reaction proceeds for 4 hrs at 90° C. in a dosed system containing a nitrogen atmosphere where after, preferably, another molar equivalent of cesium oxalate dissolved in the mixed solvent is added drop wise. Preferably, water is added to bring the ratio of dmf to water to 70:30. The reaction proceeds for a further 2 hrs. The cis-bis-chloro-(trans-l-1,2-diaminocyclohexane)platinum(II) and metal oxalate are reacted at an overall molar ratio of greater than 1:1, preferably 1:2. The overall reaction takes 4-15 hrs typically 6-8 hrs upon which time the yellow colour fades. The non-aqueous solvent is then removed by vacuum and a crude platinum(II) complex product, in this case an oxaliplatin product, is recovered. A higher yield of crude platinum(II) product may be attained by introducing the metal oxalate at a larger excess after the reaction has proceeded for at least 4 hours or at approximately half of the total reaction time. The crude product is purified by washing several times (±4 times) with small portions of cold water. The residual solid is suspended in water for approximately 15 minutes at an elevated temperature (±70° C.). The solution is then filtered and the filtrate vacuum evaporated. The residual solid is washed with small portions of dmf and finally with acetone and vacuum dried leaving a white solid, in the form of optically pure oxaliplatin, behind. The overall product yield is approximately 30%, with optical purity $\geq$99.94%.

In a second preferred embodiment of the invention, cis-bis-halogeno(trans-l-1,2-diaminocyclohexane)platinum(II), preferably where the halogen is chloride, is dissolved in a suitable non-aqueous solvent (preferably dimethylformamide (dmf)) by heating to 40 to 100° C., preferably 60 to 70° C. in an inert atmosphere to provide a hot yellow solution. A suitable organic oxalate salt, e.g. a tetra-alkyl or aryl ammonium compound such as tetraethyl, tetrapropyl or tetrabutylammonium oxalate is dissolved in the same type of solvent. The preferred organic oxalate salt is tetrabutylammonium oxalate. This solution is then added drop-wise to the hot yellow solution while stirring. Water may be added to the solution to provide a mixed solvent system. The cis-bis-chloro(trans-l-1,2-diaminocyclohexane)platinum(II) and tetrabutylammonium oxalate are reacted at a molar ratio of greater than 1:1, typically between 1:1 to 1:1, preferably between 1:1 to 1:5, most preferably 1:3. The cis-bis-chloro-(trans-l-1,2-diaminocyclohexane)platinum(II) has a solubility of 10 g/L in the solution and the tetrabutylammonium oxalate has a solubility of 300 g/L in the solution. The reaction mixture is stirred continuously at an elevated temperature of 30 to 90° C., preferably 60 to 70° C. for 4-24 hrs, preferably 6-10 hrs. The yellow solution darkens after a period of time. The solvent is removed by vacuum. A dark product recovered from the reaction is washed with cold water and ethanol (to remove any unreacted oxalate) and then centrifuged. The supernatant solvent is decanted leaving a mustard yellow solid product. The latter product is suspended in water and stirred at an elevated temperature (±70° C.) for a brief period of time (±10 minutes). The mixture is then filtered and the solvent removed by vacuum from the filtrate. In some cases a somewhat sticky product is obtained, which is washed with ethanol. The product is then washed with a small portion of dmf, rinsed with acetone and oven dried at 50° C. A pure white oxaliplatin product is thus obtained. The overall product yield is approximately 35% (based on cis-bis-chloro (trans-l-1,2-diaminocyclohexane)platinum(II)) with optical purity $\geq$99.94% and chemical purity $\geq$99.5%. The initial ethanol wash and treatment with water could be interchanged.

The tetraalkylammonium oxalate may be prepared by combining one molar equivalent of oxalic acid with two molar equivalents of a 40% standardised aqueous solution of tetraalkylammonium hydroxide. The solution is stirred at room temperature until the oxalic acid is dissolved, whereafter the pH is adjusted to 7 (using the same tetraalkylammonium hydroxide solution mentioned above). The solution is vacuum evaporated in a water bath at 40° C. until a paste was obtained. This product was then dissolved in deoxygenated dmf (50 mL), which was left to stand overnight in the dark on molecular sieves (3 Å).

The processes described above may be used to form many other platinum(II) complexes with neutral bidentate ligands (such as the neutral bidentate ligands described in PCT/IB2004/003855, the content of which is incorporated herein by reference), and makes it possible to form platinum(II) complexes with neutral bidentate ligands that contain donor atoms other than N, typically S and Se, for example:

neutral bidentate heterocyclic amines with an S donor atom, such as thioethereal S containing compounds of the general formula:

1-alkyl/aryl-2-alkylthioalkyl/aryl heterocyclic amines, particularly imidazoles or pyridines;

aminoalkylthioalkyl/aryl compounds;

dithioethers for example 2,5-dithiahexane;

diselenoethers for example 2,5-diseleno hexane; etc.

Ligands containing S or Se donor atoms cannot be used in reactions that make use of silver compounds, because these atoms react by binding very strongly with both platinum and silver ions.

The following 2-methylthioalkyl imidazole and pyridine neutral bidentate ligands:

Ligand (i) 1-methyl-2-methylthiomethyl-imidazole
Ligand (ii) 1-methyl-2-methylthioethyl-imidazole
Ligand (iii) 1-methyl-2-methylthiopropyl-imidazole
Ligand (iv) 1-butyl-2-methylthiomethyl-imidazole
Ligand (v) 1-butyl 2-methylthioethyl-imidazole
Ligand (vi) 2-methylthiomethyl-pyridine
Ligand (vii) 2-methylthioethyl-pyridine
Ligand (viii) 2-methylthiopropyl-pyridine (prepared by the methods described in J G H du Preez, T I A Gerber, W Edge, V L V Mtotywa and B J A M van Brecht. Nitrogen Reagents in Metal Ion Separation. XI. The Synthesis and Extraction Behaviour of a New NS Imidazole Derivative. Solv. Extr. & Ion Exch. (2001) 19(1), 143-154) (the content of which is incorporated herein by reference) may be used in the below method to prepare the 2-methylthioalkyl complexes of imidazole and pyridine (i) to (v) mentioned below.

Examples of 2-methylthioalkyl complexes of imidazole prepared by the above method are reflected in the structural Formula (I) below where $R_1$ and $R_2$ may be selected from alkyl (e.g. $CH_3$, $C_2H_5$ etc.) and aryl (e.g. phenyl) groups. Typical 2-methylthioalkyl complexes of imidazole are complexes (i) to (v) below:

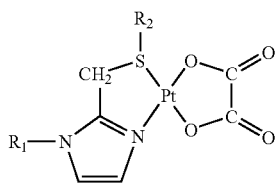

Formula (I)

Complex (i) $R_1=CH_3$ $R_2=CH_3$
Complex (ii) $R_1=CH_3$ $R_2=C_2H_5$
Complex (iii) $R_1=CH_3$ $R_2=C_3H_7$
Complex (iv) $R_1=C_4H_9$ $R_2=CH_3$
Complex (v) $R_1=C_4H_9$ $R_2=C_2H_5$ The chemical names for the complexes (i) to (v) are:
Complex (i) oxalato(1-methyl-2-methylthiomethyl-imidazole)platinum(II)
Complex (ii) oxalato(1-methyl-2-methylthioethyl-imidazole)platinum(II)
Complex (iii) oxalato(1-methyl-2-methylthiopropyl-imidazole)platinum(II)
Complex (iv) oxalato(1-butyl-2-methylthiomethyl-imidazole)platinum(II)
Complex (v) oxalato(1-butyl-2-methylthioethyl-imidazole) platinum(II).

Examples of 2-methylthioalkyl complexes of pyridine of the invention are reflected in the structural Formula (II) below where $R_2$ may be selected from alkyl (e.g. $CH_3$, $C_2H_5$ etc.) and aryl (e.g. phenyl) groups. Typical 2-methylthioalkyl complexes of pyridine are compounds (vi) to (viii) below:

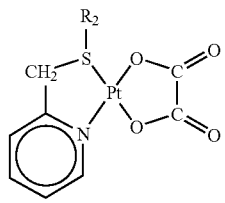

Formula (II)

Complex (vi) $R_2=CH_3$
Complex (vii) $R_2=C_2H_6$
Complex (viii) $R_2=C_3H_7$

The chemical names for the complexes (vi) to (viii) are:
Complex (vi) oxalato(2-methylthiomethyl-pyridine)platinum(II)
Complex (vii) oxalato(2-methylthioethyl-pyridine)platinum (II)
Complex (viii) oxalato(2-methylthiopropyl-pyridine)platinum(II).

2-methylthioalkyl complexes of imidazole and pyridine mentioned above have been shown to have anti-cancer properties The following ligands:
Ligand (ix) 1-amino-2-thiomethyl-ethane
Ligand (x) 1-amino-2-thioethyl-ethane may be used to prepare the following aliphatic aminothioether complexes of Pt(II)oxalate:
Complex (ix) oxalato(1-amino-2-thiomethyl-ethene)platinum(II)
Complex (x) oxalato(1-amino-2-thioethyl-ethane)platinum (II).

New halogenoplatinum(II) complexes which may be used in the methods of this invention include halogenoplatinum(II) complex having a neutral bidentate ligand that contains donor atoms other than N, typically S and Se, for example:

neutral bidentate heterocyclic amines with an S donor atom, such as thioetherial S containing compounds of the general formula:

1-alkyl/aryl-2-alkylthioalkyl/aryl heterocyclic amines, particularly imidazoles or pyridines;
aminoalkylthioalkyl/aryl compounds;
dithioethers for example 2,5-dithiahexane;

diseleno ethers for example 2,5-diseleno hexane; etc. is prepared. The neutral bidentate ligand may be selected from any of ligands i) to x) above. The halogenoplatinum(II) complex may be prepared by reacting a platinum(II) compound such as $K_2PtX_4$ where X is a halide such Cl, Br or I, preferably Cl with a suitable neutral bidentate ligand. Typical halogenoplatinum (II) complexes so formed are reflected in the structural Formula (III) below where $R_1$ and $R_2$ may be selected from alkyl (e.g. $CH_3$, $C_2H_5$ etc.) and aryl (e.g. phenyl) groups.

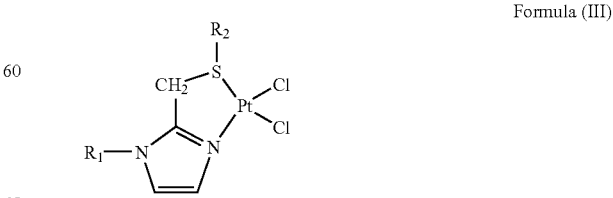

Formula (III)

Complex (xi) $R_1=CH_3$ $R_2=CH_3$
Complex (xii) $R_1=CH_3$ $R_2=C_2H_5$

Complex (xiii) $R_1=CH_3$ $R_2=C_3H_7$
Complex (xiv) $R_1=C_4H_9$ $R_2=CH_3$
Complex (xv) $R_1=C_4H_9$ $R_2=C_2H_5$ The chemical names for the complexes (xi) to (xv) are:
Complex (xi) bis-chloro-(1-methyl-2-methylthiomethyl-imidazole)platinum(II)
Complex (xii) bis-chloro-(1-methyl-2-methylthioethyl-imidazole)platinum(II)
Complex (xiii) bis-chloro-(1-methyl-2-methylthiopropyl-imidazole)platinum(II)
Complex (xiv) bis-chloro-(1-butyl-2-methylthiomethyl-imidazole)platinum(II)
Complex (xv) bis-chloro-(1-butyl-2-methylthioethyl-imidazole)platinum(II).

A preferred halogenoplatinum(II) complex is bis-chloro-(1-methyl-2-methylthiomethyl-imidazole)platinum(II). This complex has been shown to have exceptional anti-cancer properties and this invention extends to the application of these halogenoplatinum(II) complexes as new anticancer agents which may be used in methods of treating cancer in patients, and in methods of manufacturing medicaments for treating cancer in patients.

The above methods are advantageous over prior art methods in that:
(i) They do not result in the formation of insoluble silver chloride which must be removed by filtration.
(ii) They do not use silver, and therefore the contaminants associated with the silver method are absent.
(iii) The metastable Pt(trans-l-1,2-diaminocyclohexane)$(H_2O)_2^{2+}$ species formed as an intermediate in the silver method which readily leads to hydroxo Pt(II) species, is not present.
(iv) No free oxalic acid is used in the reaction with the Pt(II) compound, thus its contamination is excluded.
(v) The use of the non-aqueous solvent and mixed solvent having a majority of an aprotic solvent (dmf) greatly lowers the activity of $H_2O$ in the solvent thus greatly limits reactions such as hydrolysis and oxo bridge formation.
(vi) The time to reach the equilibrium of the reaction is significantly reduced at the elevated temperature.

The invention will now be described in more detail with reference to the following non-limiting examples. In all examples, 1,2-diaminocyclohexane=1,2-diaminocyclohexane and dmf=dimethylformamide. Solvents used in the examples are deoxygenated.

EXAMPLE 1

This example shows a method for preparing optically pure Pt(trans-l-1,2-diaminocyclohexane)$Cl_2$ which is an intermediate compound in the process of the present invention.

Trans-1,2-diaminocyclohexane (5.70 g, 50 mmol) is dissolved in water (10 mL). l-tartaric acid (3.75 g, 25 mmol) is added incrementally to the solution while continuously stirring and once completely added to the solution, the mixture is heated to 90° C. When all the tartaric acid is dissolved, glacial acetic acid (5 mL, 85 mmol) is added dropwise while stirring. The mixture is heated for 1 hour at 90° C. whereafter it is cooled to room temperature. The resultant white l-1,2-diaminocyclohexane-tartrate is filtered and washed twice with cold water (5 mL), 3 times with methanol (5 mL) and oven dried. The salt is recrystallized out of hot water and cooled overnight at 5° C.

The recrystallized l-1,2-diaminocyclohexane-tartrate (18.9 g, 72.62 mmol) is added to 4 equivalents of sodium hydroxide (11.62 g, 290.49 mmol) dissolved in water (100 mL). Once the amine has dissolved it is extracted 5 times with 100 mL portions of dichloromethane. The extracted dichloromethane portions are added together and dried with anhydrous sodium sulphate. Most of the solvent is removed by vacuum distillation. The last portion of solvent is removed in atmospheric pressure to avoid the amine from distilling under vacuum using an air condenser. Yield: 23% (overall).

The optically pure amine was then applied to prepare optically pure Pt(trans-l-1,2-diaminocyclohexane)$Cl_2$ by a method described in Inorganica Chimica Acta (1985) 108: pp 63-66 (the content of which is incorporated herein by reference), from pure $K_2PtCl_4$.

EXAMPLE 2

This example shows a first embodiment of the invention for producing oxaliplatin by reacting a halogenoplatinum(II) complex containing a neutral bidentate ligand, with a metal oxalate in a mixed solvent system.

Optically pure Pt(trans-1,2-diaminocyclohexane)$Cl_2$ (0.508 g, 1.3 mmol) was dissolved in dmf (93 mL) at 90° C. The solvent ratio was adjusted to 87:13 dmf:water by adding 14 mL water. One equivalent of cesium oxalate (0.508 g, 1.3 mmol) was dissolved in 4 mL of solvent containing 1 mL dmf and 3 mL water. This solution was added drop-wise while stirring to the yellow Pt(trans-l-1,2-diaminocyclohexane)$Cl_2$ solution. The reaction mixture was stirred continuously for 6 hours at 90° C. in a closed system containing a nitrogen atmosphere after which the solvent was removed by vacuum. The resultant light yellow solid was washed (4 times) with small portions (4 mL) of cold water. The residual solid was suspended in water for 10 minutes at 70° C. The solution was filtered and the solvent removed by vacuum. The residual cream solid was washed (twice) with small portions of dmf (2 mL), finally with acetone and vacuum dried. The white solid product proved to be pure oxaliplatin. Optical purity ≧99.94%. Overall yield from Pt(trans-l-1,2-diaminocyclohexane)$Cl_2$ ~25%.

EXAMPLE 3

This example shows a first embodiment of the invention for producing oxaliplatin by reacting a halogenoplatinum(II) complex containing a neutral bidentate ligand, with a metal oxalate in a mixed solvent system.

Optically pure Pt(trans-l-1,2-diaminocyclohexane)$Cl_2$ (1.017 g, 2.68 mmol) was dissolved in dmf (176 mL) at 90° C. whereafter 17 mL water was added. One equivalent of cesium oxalate (0.947 g, 2.68 mmol) was dissolved in 13 mL of solvent containing 3 mL dmf and 10 mL water. This solution was added drop-wise while stirring, to the yellow Pt(trans-l-1,2-diaminocyclohexane)$Cl_2$ solution. The overall solvent ratio achieved at this point was 87:13 (dmf:water). The reaction mixture was stirred continuously for 4 hours at 90° C. in a closed system containing a nitrogen atmosphere whereafter another equivalent of cesium oxalate dissolved in 10.6 mL solvent, containing 2.6 mL dmf and 8 mL water, was added drop-wise. More water (30 mL) was added to change the solvent ratio to 70:30 dmf:water. The reaction mixture was again stirred for a further 2 hours after which the solution was allowed to cool and the solvent removed by vacuum. The resultant pale solid was washed (4 times) with small portions (8 mL) of cold water. The residual solid was suspended in water for 10 minutes at 70° C. The solution was filtered and the solvent removed by vacuum. The residual cream solid was washed (twice) with small portions of dmf (4 mL), finally with acetone and vacuum dried. The white solid product proved to be pure oxaliplatin. Optical purity ≧99.94%. Overall yield from Pt(trans-l-1,2-diaminocyclohexane)$Cl_2$ ~30%.

EXAMPLE 4

This example shows a method for preparing tetrabutylammonium oxalate which is used as an intermediate in a second embodiment of the invention for producing oxaliplatin.

1 molar equivalent of oxalic acid (6.5 g, 52.15 mmol) was added to 2 molar equivalents of a 40% standardised aqueous solution of tetrabutylammonium hydroxide (104.2 mmol). The solution was then stirred at room temperature until the oxalic acid had dissolved, whereafter the pH was adjusted to 7 (by the addition of tetrabutylammonium hydroxide). The solution was vacuum evaporated in a waterbath at 40° C. until a paste was obtained. The product was dissolved in dry, deoxygenated dmf (50 mL) which was left on molecular sieves (3 Å) overnight in the dark. This standard solution of the oxalate was used as such.

EXAMPLE 5

This example shows a second embodiment of the invention for producing oxaliplatin by reacting a halogenoplatinum(II) complex containing a neutral bidentate ligand, with an organic oxalate in a non-aqueous solvent.

Pt(trans-l-1,2-diaminocyclohexane)$Cl_2$ (0.520 g, 1.37 mmol) was dissolved in 80 mL dmf at 70° C. to which was added drop-wise while stirring 1.2 equivalents of a 1.291M dmf solution of tetrabutylammonium oxalate (1.275 mL, 1.65 mmol). The yellow solution was stirred for 6 hours at 70° C. in a closed system. During the reaction the solution darkened to brown. After reacting the solution for 6 hours the solvent was removed by vacuum. The remaining solid was suspended in 20 mL of water and stirred for 10 minutes at 70° C. The mixture was filtered and the solvent was vacuum removed from the filtrate. The residual solid was washed twice with ethanol (2×20 mL) and finally with 2 mL of dmf. The white product was dried at 50° C. The optical purity was ≧99.94% and chemical purity ≧99.5%. Overall yield 30%.

EXAMPLE 6

This example shows a second embodiment of the invention for producing oxaliplatin by reacting a halogenoplatinum(II) complex containing a neutral bidentate ligand, with an organic oxalate salt in a mixed solvent system.

Pt(trans-l-1,2-diaminocyclohexane)$Cl_2$ (1.040 g, 2.74 mmol) was dissolved in 140 mL dmf at 60° C. 1.5 equivalents of a 1.291M dmf solution of tetrabutylammonium oxalate (3.184 mL, 4.11 mmol) was added drop-wise to the yellow Pt(trans-l-1,2-diaminocyclohexane)$Cl_2$ solution. Distilled water (7.6 mL) was added such that the solvent ratio was adjusted to 95:5 dmf-water. The mixture was stirred constantly for 6 hours at 60° C. in a closed system under nitrogen. During the reaction the colour of the solution changed from yellow to brown. On completion of the reaction time the solution was cooled and the solvent removed by vacuum. The remaining solid was suspended in 40 mL of distilled water and stirred for 10 minutes at 70° C. The mixture was filtered and the solvent removed from the filtrate by vacuum. The solid residue was washed twice with ethanol (2×50 mL) and centrifuged. The residual solid was then washed twice with 4 mL of dmf, rinsed once with acetone and oven dried at 50° C. The optical purity was ≧99.94% and chemical purity ≧99.5%. Overall yield 35%.

EXAMPLE 7

This example shows a scaled-up second embodiment of the invention for producing oxaliplatin by reacting a halogenoplatinum(II) complex containing a neutral bidentate ligand, with an organic oxalate salt in a mixed solvent system.

Pt(trans-l-1,2-diaminocyclohexane)$Cl_2$ (4.0189, 10.57 mmol) was dissolved in dmf (490 mL) to which was added 50 mL water. Three equivalents of tetrabutylammonium oxalate in dmf solution (26 ml 31.71 mmol) was added drop-wise while stirring to the yellow Pt(trans-l-1,2-diaminocyclohexane)$Cl_2$ solution. The mixture was stirred for 4 hours at approximately 65° C. whereafter a further equivalent of Pt(trans-l-1,2-diaminocyclohexane)$Cl_2$ (3.998 g, 10.52 mmol) dissolved in dmf (560 mL) and 58 mL water was added. The mixture was further reacted at 65° C. such that the total reaction time was 8 hours.

The solvent of the reaction mixture was evaporated by vacuum. The residual solid was stirred in 320 mL of water for 15 minutes at 70° C. In a nitrogen atmosphere. The suspension was filtered and the solvent vacuum removed from the filtrate. The resulted solid was washed twice with 60 mL of ethanol and twice with 15 mL of dmf. All the above washings were discarded. The resulting cream solid was recrystallized from hot water in a nitrogen atmosphere. The white crystalline product was optically pure (≧99.94%). The chemical purity was ≧99.5%. Overall yield: 35%.

EXAMPLE 8

This example shows a method for preparing bis-chloro-(1-methyl-2-methylthiomethyl-imidazole)platinum(II) which is used as an intermediate in methods of the invention for producing a platinum(II) complex.

$K_2PtCl_4$ (1.012 g, (2.4 mmol) was dissolved in 20 mL water to which was added dropwise an acetone solution (2 mL) of 1-methyl-2-methylthiomethyl-imidazole (0.392 g, 2.7 mmol). The reaction mixture was stirred overnight at room temperature whereafter the resultant precipitate was filtered, the product washed once with cold water (3 mL) and oven dried at 55° C. Chemically pure cream coloured bis-chloro-(1-methyl-2-methylthiomethyl-imidazole)platinum (II) was produced in an 88% yield (0.876 g).

EXAMPLE 9

Anticancer testing on the halogenoplatinum(II) complex of Example 8 was performed and compared with cisplatin. The percentages inhibition of Pt(mmtei)$Cl_2$ (where mmtei=1-methyl-2-methylthioethyl-imidazole) on colon cancer cells were 92.8% and 97.0% at 10 and 100 μM solutions. The corresponding values for cisplatin are 85.6% and 93.2%. The corresponding data on cervical cancer cells are 88.5 and 95.9% at 10 and 100 μM solutions. The corresponding values for cisplatin are 85.4 and 95% respectively. A further study in which 100 μM solutions were used in a medium containing 10 mM glutathione, the halogenoplatinum(II) complex performed even better, viz. 98.2% inhibition on colon cells (cisplatin 48.0%); 99.3% on cervical cancer cells (cisplatin 58.6%); and 66.1% on breast cancer cells (cisplatin 14%).

The invention claimed is:

1. A method for the preparation of a platinum(II) complex containing a neutral bidentate ligand, the method including the step of reacting a halogenoplatinum(II) complex containing a neutral bidentate ligand with a water soluble metal oxalate other than silver oxalate in a solvent, wherein the neutral bidentate ligand is reacted with the oxalate at a molar ratio of greater than 1:1.

2. The method according to claim 1, wherein the oxalate is a metal oxalate selected from rubidium oxalate or cesium oxalate.

3. The method according to claim 1, wherein the halogenoplatinum(II) complex containing a neutral bidentate ligand is reacted with the oxalate at a molar ratio of between 1:1 and 1:15.

4. The method according to claim 3, wherein the halogenoplatinum(II) complex containing a neutral bidentate ligand is reacted with oxalate at a molar ratio of between 1:1 and 1:5.

5. The method according to claim 1, wherein the solvent is a mixed solvent system.

6. The method according to claim 5, wherein the mixed solvent system is a mixture of an amide and water.

7. The method according to claim 6, wherein the amide is dimethylformamide (dmf).

8. The method according to claim 7, wherein the ratio of dmf to water is 60:40 to 90:10 by volume.

9. The method according to claim 8, wherein the ratio of dmf to water is 70:30 by volume to 90:10 by volume.

10. The method according to claim 1, wherein the solubility of the metal oxalate in the solvent is greater than 2 g/L.

11. The method according to claim 10, wherein the solubility of the metal oxalate in the solvent is greater than 3 g/L.

12. The method according to claim 11, wherein the solubility of the metal oxalate in the solvent is about 5 g/L.

13. The method according to claim 1, wherein the halogenoplatinum(II) complex containing a neutral bidentate ligand is dissolved in a non-aqueous solvent and thereafter water is added to provide a solvent which is a mixture of non-aqueous solvent and water.

14. The method according to claim 1, wherein the metal oxalate is dissolved in a mixture of non-aqueous solvent and water and added to a solvent containing the halogenoplatinum (II) complex containing a neutral bidentate ligand.

15. The method according to claim 1, wherein the reaction takes place at a temperature in the range of 40 to 100° C.

16. The method according to claim 15, wherein the reaction takes place at a temperature in the range of 80 to 100° C.

17. The method according to claim 16, wherein the reaction takes place at a temperature of 90° C.

18. The method according to claim 1, wherein the halogenoplatinum(II) complex is bis-chloro-(trans-l-1,2-diaminocyclohexane)platinum(II).

19. The method according to claim 18, wherein the halogenoplatinum(II) complex is cis-bis-chloro-(trans-l-1,2-diaminocyclohexane)platinum(II).

20. A method for the preparation of a platinum(II) complex containing a neutral bidentate ligand, the method including the step of reacting a halogenoplatinum(II) complex containing a neutral bidentate ligand with an organic oxalate salt in a solvent.

21. The method according to claim 20, wherein the halogenoplatinum(II) complex containing a neutral bidentate ligand is reacted with the oxalate at a molar ratio of greater than 1:1.

22. The method according to claim 21, wherein the halogenoplatinum(II) complex containing a neutral bidentate ligand is reacted with the oxalate at a molar ratio of between 1:1 and 1:15.

23. The method according to claim 22, wherein the halogenoplatinum(II) complex containing a neutral bidentate ligand is reacted with oxalate at a molar ratio of between 1:1 and 1:5.

24. The method according to claim 20, wherein the organic oxalate salt is a tetra-alkyl or aryl ammonium compound.

25. The method according to claim 24, wherein the organic oxalate salt is a tetramethylammonium, tetraethylammonium, tetrapropylammonium, tetrabutylammonium or tetraphenylphosphonium oxalate.

26. The method according to claim 25, wherein the organic oxalate salt is tetrabutylammonium oxalate.

27. The method according to claim 20, wherein the solvent is a mixed solvent system or a non-aqueous solvent.

28. The method according to claim 27, wherein the solvent is a mixture of a non-aqueous solvent and water.

29. The method according to claim 28, wherein the non-aqueous solvent is an amide.

30. The method according to claim 29, wherein the amide is dimethylformamide (dmf).

31. The method of claim 30, wherein the dmf and water are at a ratio of 90:10 by volume to 95:5 by volume.

32. The method according to claim 27, wherein the solvent is a non-aqueous solvent.

33. The method according to claim 32, wherein the non-aqueous solvent is an amide.

34. The method according to claim 33, wherein the amide is dimethylformamide (dmf).

35. The method according to claim 20, wherein the organic oxalate salt has a solubility in the solvent of greater than 2 g/L.

36. The method according to claim 35, wherein the organic oxalate salt has a solubility in the solvent of greater than 10 g/L.

37. The method according to claim 36, wherein the organic oxalate salt has a solubility in the solvent of greater than 50 g/L.

38. The method according to claim 37, wherein the organic oxalate salt has a solubility of greater than 100 g/L.

39. The method according to claim 20, wherein the halogenoplatinum(II) complex containing a neutral bidentate ligand is dissolved an non-aqueous solvent and the organic oxalate salt is dissolved in a non-aqueous solvent and added to the solvent containing the halogenoplatinum(II) complex containing a neutral bidentate ligand.

40. The method according to claim 20, wherein the reaction takes place at a temperature of 30 to 100° C.

41. The method according to claim 40, wherein the reaction takes place at a temperature of 50 to 70° C.

42. The method according to claim 20, wherein water is added to solvent after the halogenoplatinum(II) complex has been dissolved in the solvent.

43. The method according to claim 20, wherein the reaction takes place from 6 to 10 hours.

44. The method according to claim 20, wherein the halogenoplatinum(II) complex is bis-chloro-(trans-l-1,2-diaminocyclohexane)platinum(II).

45. The method according to claim 20, wherein the platinum(II) complex containing a neutral bidentate ligand is oxaliplatin.

46. The method according to claim 1, wherein the platinum (II) complex containing a neutral bidentate ligand is oxaliplatin.

47. A method for the preparation of a platinum(II) complex containing a neutral bidentate ligand, the method including the step of reacting a halogenoplatinum complex containing a neutral bidentate ligand with an oxalate salt in a solvent, where the solvent is a non-aqueous solvent or a mixed solvent system.

48. The method according to claim 47, wherein the halogenoplatinum complex containing a neutral bidentate ligand is a halogenoplatinum(II) complex containing a neutral bidentate ligand.

49. The method according to claim 47, wherein the halogenoplatinum complex containing a neutral bidentate ligand is reacted with the oxalate at a molar ratio of greater than 1:1.

50. The method according to claim 49, wherein the halogenoplatinum complex containing a neutral bidentate ligand is reacted with the oxalate at a molar ratio of between 1:1 and 1:15.

51. The method according to claim 50, wherein the halogenoplatinum complex containing a neutral bidentate ligand is reacted with oxalate at a molar ratio of between 1:1 and 1:5.

52. The method according to claim 47, wherein the reaction takes place at a temperature in the range of 40 to 100° C.

53. The method according to claim 52, wherein the reaction takes place at a temperature in the range of 60 to 90° C.

54. The method according to claim 47, wherein the non-aqueous solvent is an organic liquid.

55. The method according to claim 54, wherein the organic liquid is an amide.

56. The method according to claim 55, wherein the amide is dimethylformamide (dmf).

57. The method according to claim 47, wherein the neutral bidentate ligand is an amine.

58. The method according to claim 57, wherein the amine is cyclohexane-1-2-diamine.

59. The method according to claim 47, wherein the neutral bidentate ligand contains donor atoms other than N, or N together with a donor atom other than N.

60. The method according to claim 59, wherein the neutral bidentate ligand contains S or Se.

61. The method according to claim 60, wherein the neutral bidentate ligand is a heterocyclic amine with a S donor atom.

62. The method according to claim 61, wherein the neutral bidentate heterocyclic amine contains a thioethereal S donor atom.

63. The method according to claim 62, wherein the neutral bidentate ligand is a 1-alkyl/aryl-2-alkylthioalkyl/aryl heterocyclic amine.

64. The method according to claim 63, wherein the heterocyclic amine contains an imidazole or pyridine group.

65. The method according to claim 64, wherein the neutral bidentate ligand is:
Ligand (i) 1-methyl-2-methylthioethyl-imidazole,
Ligand (ii) 1-methyl-2-methylthiopropyl-imidazole,
Ligand (iii) 1-butyl-2-methylthiomethyl-imidazole,
Ligand (iv) 1-methyl-2-methylthiomethyl-imidazole,
Ligand (v) 1-butyl-2-methylthioethyl-imidazole,
Ligand (vi) 2-methylthiomethyl-pyridine,
Ligand (vii) 2-methylthioethyl-pyridine, or
Ligand (viii) 2-methylthiopropyl-pyridine.

66. The method according to claim 59, wherein the neutral bidentate ligand is an aminoalkylthioalkyl/aryl compound.

67. The method according to claim 66, wherein the neutral bidentate ligand is:
Ligand (ix) 1-amino-2-thiomethyl-ethane, or
Ligand (x) 1-amino-2-thioethyl-ethane.

68. The method according to claim 67, wherein the neutral bidentate ligand is a dithioether.

69. The method according to claim 68, wherein the neutral bidentate ligand is Ligand (xi) 2,5-dithiahexane.

70. The method according to claim 59, wherein the neutral bidentate ligand is a diselenoether.

71. The method according to claim 70, wherein the neutral bidentate ligand is Ligand (xii) 2,5-diselenohexane.

72. The method according to claim 47 wherein the halogen in the halogenoplatinum(II) complex is Cl, Br or I.

73. The method according to claim 72, wherein the halogen in the halogenoplatinum(II) complex is Cl.

74. The method according to claim 47, wherein the halogenoplatinum(II) complex containing a neutral bidentate ligand is optically pure in the case of chiral compounds.

75. The method according to claim 47, wherein the oxalate is a metal oxalate or an organic oxalate salt.

76. The method according to claim 75, wherein the oxalate is a metal oxalate and the solvent is a mixed solvent system.

77. The method according to claim 76, wherein the metal oxalate is an alkali metal oxalate.

78. The method according to claim 77, wherein the metal oxalate is rubidium or cesium oxalate.

79. The method according to claim 78, wherein the metal oxalate is cesium oxalate.

80. The method according to claim 76, wherein the mixed solvent system is a mixture of an amide and water.

81. The method according to claim 80, wherein the amide is dimethylformamide (dmf).

82. The method according to claim 81, wherein the ratio of dmf to water is 60:40 to 90:10 by volume.

83. The method according to claim 82, wherein the ratio of dmf to water is 70:30 by volume to 90:10 by volume.

84. The method according to claim 76, wherein the halogenoplatinum complex containing a neutral bidentate ligand is dissolved in the organic liquid and thereafter water is added to provide a solvent which is a mixture of organic liquid and water.

85. The method according to claim 76, wherein the metal oxalate is dissolved in a mixture of organic liquid and water and added to a solvent containing the halogenoplatinum complex containing a neutral bidentate ligand.

86. The method according to claim 76, wherein the reaction takes place at a temperature in the range of 40 to 100° C.

87. The method according to claim 86, wherein the reaction takes place at a temperature in the range of 80 to 100° C.

88. The method according to claim 87, wherein the reaction takes place at a temperature of 90° C.

89. The method according to claim 76, wherein the halogenoplatinum complex is bis-chloro-(trans-l-1,2-diaminocyclohexane)platinum(II).

90. The method according to claim 89, wherein the halogenoplatinum complex is cis-bis-chloro-(trans-l-1,2-diaminocyclohexane)platinum(II).

91. The method according to claim 47, wherein the oxalate is an organic oxalate salt.

92. The method according to claim 91, wherein the organic oxalate salt is a tetra-alkyl or aryl ammonium compound.

93. The method according to claim 92, wherein the organic oxalate salt is a tetramethylammonium, tetraethylammonium, tetrapropylammonium, tetrabutylammonium or tetraphenylphosphonium oxalate.

94. The method according to claim 93, wherein the organic oxalate salt is tetrabutylammonium oxalate.

95. The method according to claim 91, wherein the solvent is a mixed solvent system.

96. The method according to claim 95, wherein the mixed solvent system includes a non-aqueous solvent which is dimethylformamide (dmf).

97. The method of claim 96, wherein the dmf and water are at a ratio of 90:10 by volume to 95:5 by volume.

98. The method according to claim 91, wherein the solvent is a non-aqueous solvent.

99. The method according to claim 91, wherein the halogenoplatinum complex containing a neutral bidentate ligand is dissolved in a non-aqueous solvent and the organic oxalate salt is dissolved in a non-aqueous solvent and added to the solvent containing the halogenoplatinum complex containing a neutral bidentate ligand.

100. The method according to claim 91, wherein the reaction takes place at a temperature of 50 to 70° C.

101. The method according to claim 100, wherein the reaction takes place at a temperature of 60° C.

102. The method according to claim 91, wherein water is added to a non-aqueous solvent after the halogenoplatinum complex has been dissolved in the non-aqueous solvent.

* * * * *